United States Patent
Hochman et al.

(10) Patent No.: US 6,966,899 B2
(45) Date of Patent: *Nov. 22, 2005

(54) HAND-PIECE FOR INJECTION DEVICE WITH A RETRACTABLE AND ROTATING NEEDLE

(75) Inventors: Mark N. Hochman, Lake Success, NY (US); David Pettinato, Schaumburg, IL (US); Troy W. Livingston, North Brook, IL (US)

(73) Assignee: Milestone Scientific, Inc., Livingston, NJ (US)

( * ) Notice: Subject to any disclaimer, the term of this patent is extended or adjusted under 35 U.S.C. 154(b) by 164 days.

This patent is subject to a terminal disclaimer.

(21) Appl. No.: 10/209,354

(22) Filed: Jul. 31, 2002

(65) Prior Publication Data

US 2002/0188258 A1    Dec. 12, 2002

Related U.S. Application Data

(62) Division of application No. 09/506,484, filed on Feb. 17, 2000, now Pat. No. 6,428,517.

(60) Provisional application No. 60/133,397, filed on May 10, 1999, provisional application No. 60/173,374, filed on Dec. 28, 1999.

(51) Int. Cl.[7] .......................... A61M 5/32; A61M 5/00
(52) U.S. Cl. ................... 604/198; 604/188; 604/192
(58) Field of Search ................ 604/110, 164.08, 604/177, 192, 198, 263, 188, 164.12, 171, 604/164.01, 165.01

(56) References Cited

U.S. PATENT DOCUMENTS

| | | | | |
|---|---|---|---|---|
| 5,219,339 A | * | 6/1993 | Saito | 604/198 |
| 5,429,613 A | * | 7/1995 | D'Amico | 604/198 |
| 5,921,982 A | * | 7/1999 | Lesh et al. | 606/41 |
| 5,951,529 A | * | 9/1999 | Utterberg | 604/263 |
| 6,102,887 A | * | 8/2000 | Altman | 604/22 |
| 6,726,658 B2 | * | 4/2004 | Hochman | 604/164.08 |

* cited by examiner

*Primary Examiner*—Michael J. Hayes
(74) *Attorney, Agent, or Firm*—Gottlieb Rackman & Reisman, P.C.

(57) ABSTRACT

An injection device is arranged and constructed to simultaneously rotate a needle during its forward translation as a therapeutic agent such as a liquid is ejected therefrom. In one embodiment the injection device is an automatic device including a pump forcing the liquid through a tube to a hand-piece. The needle has a first position in which it is disposed within a housing of the hand-piece, and a second position in which the needle extends outwardly of the hand-piece so that it can be used to eject the liquid, with the needle being automatically uni- or bi-directionally rotated as it is advanced between the first and second positions. In an alternate positions a syringe is provided with a barrel, a plunger extending into the barrel to eject the liquid through the needle, and a plunger which is pushed into the barrel by the operator.

11 Claims, 7 Drawing Sheets

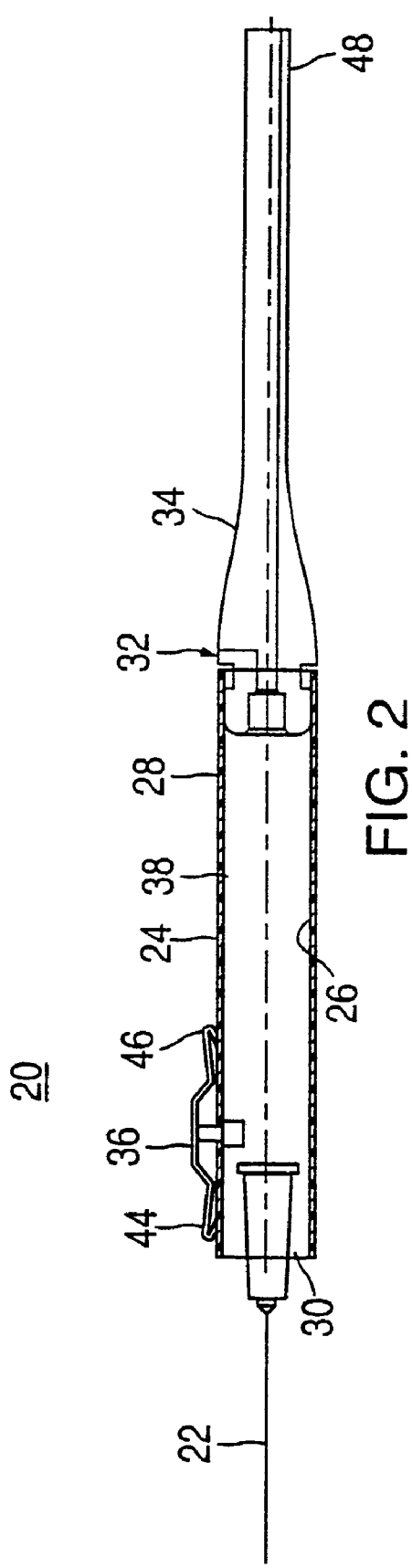
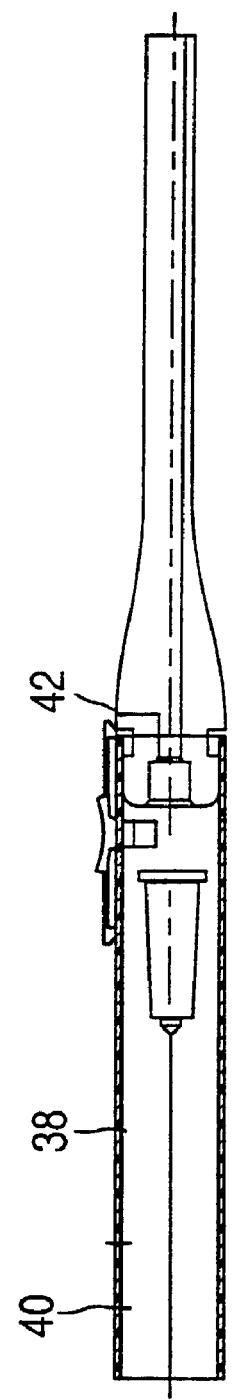
FIG. 2
FIG. 3

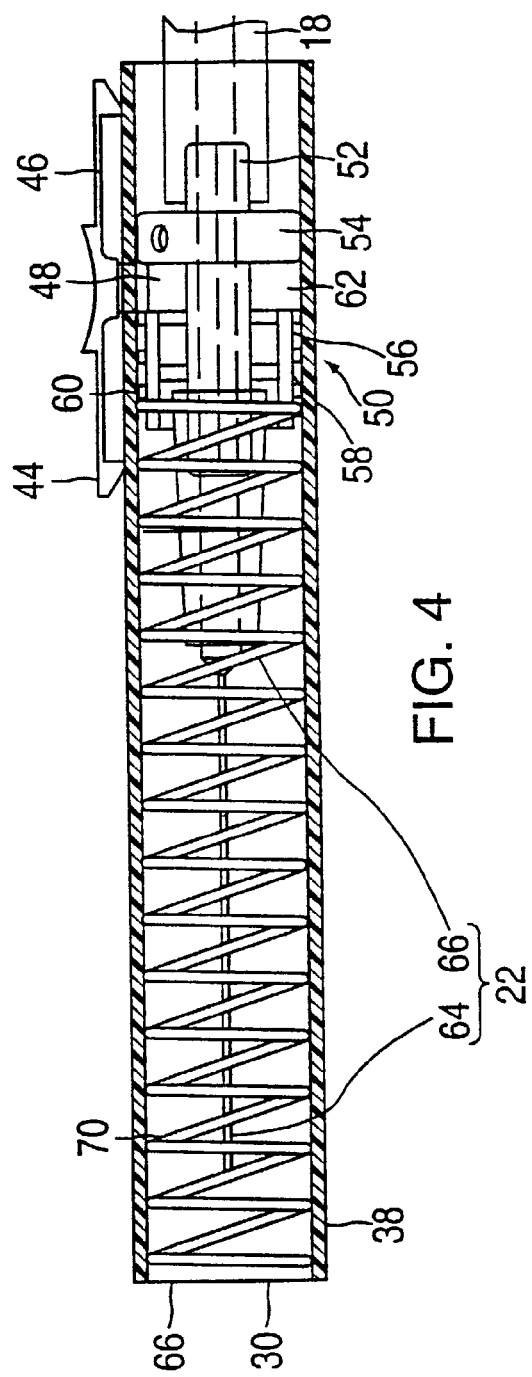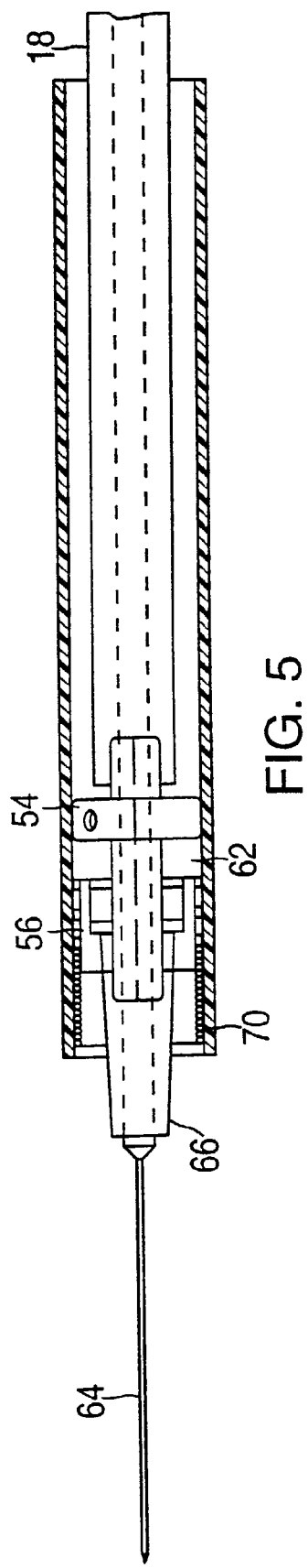

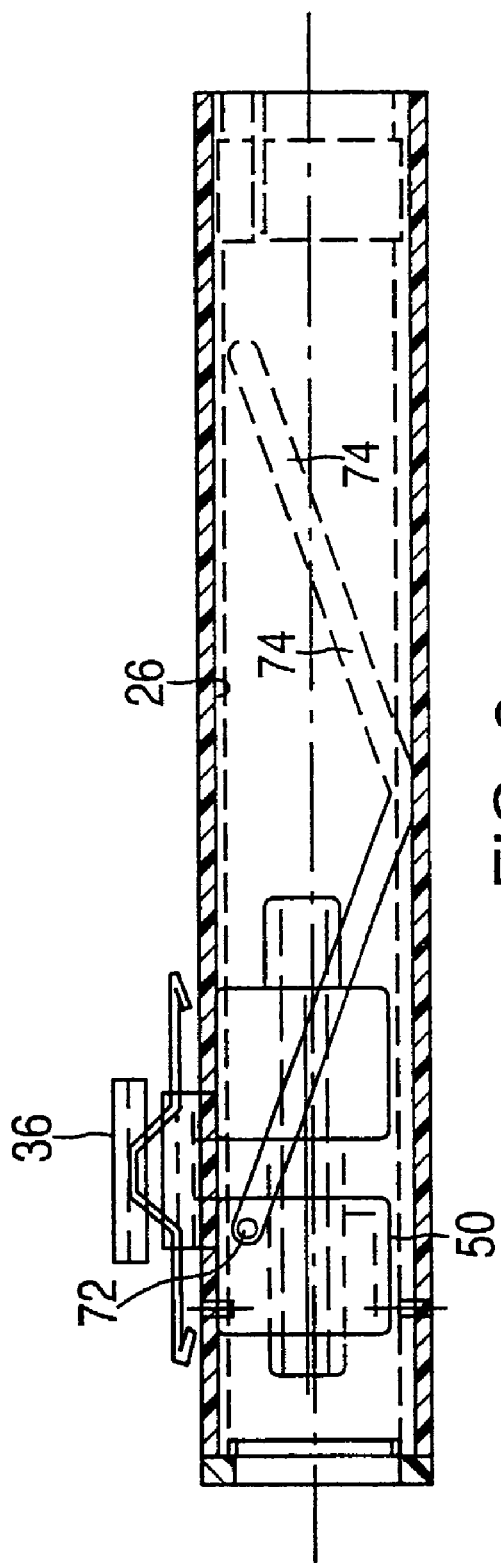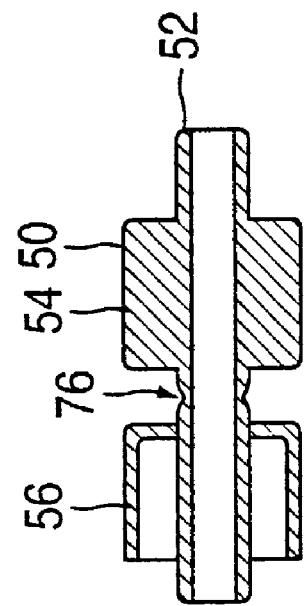

HAND-PIECE FOR INJECTION DEVICE WITH A RETRACTABLE AND ROTATING NEEDLE

RELATED APPLICATIONS

This application claims priority to provisional applications Ser. No. 60/133,397 filed May 10, 1999 and Ser. No. 60/173,374 filed Dec. 28, 1999.

This application is a divisional of application Ser. No. 09/506,484 filed Feb. 17, 2000, now U.S. Pat. No. 6,428,517, incorporated herein by reference.

BACKGROUND OF THE INVENTION

I. Field of the Invention

This invention pertains to a hand-piece for an injection device or similar apparatus used to inject a therapeutic fluid into human or animal tissues, and more particularly to a hand-piece which includes a needle movable along a longitudinal axis, which needle is optionally rotating about said axis as well.

II. Description of the Prior Art

It is well documented in both dental and medical literature that pain, tissue damage and post-op complications have long been tolerated as negative side effects from the use of existing hypodermic drug delivery injection systems. The pain and tissue damage are as a direct result of uncontrolled flow rate in conjunction with excessive pressures created during the administration of drug solutions within the tissues. Subjective pain response of a patient has been demonstrated to be minimized at specific flow rates during the administration of a drug. Also, it has been scientifically demonstrated that particular pressures (excessive without occlusion, per se) for a specific tissue type will cause damage. It is therefore critical that a specific flow rate in conjunction with a specified pressure range be maintained during the delivery of fluids (drugs) when a subcutaneous injection is given preventing subjective pain response as well as tissue damage. It is also necessary that this system have the capability to aspirate under controlled conditions of rate and pressure to avoid the same negative side effects during fluid movement. U.S. Pat. No. 5,180,371 to Spinello, incorporated herein by reference, presented an invention which allowed a rate to be set for the drug via a hypodermic needle disposed in a hand-piece.

One of the goals of dentistry and medicine should be to administer care to patients in the most humane and painless manner. The sine qua non of any treatment is to produce a desired result without causing damage or pain to the individual. Therefore there is an important need in all fields of surgery for an injection system which can be used to administer a fluid while causing substantially no pain or tissue damage to the patient.

Another goal of dentistry and medicine in general is to insure that during any procedure involving interaction between a dentist or other care giver and a patient, utmost care is taken to protect the care giver from injury and/or infection with diseases.

The use of hollow-core needles is the standard in drug delivery in medicine and dentistry. The use of the hollow-core needle dates back over 150 years when Charles Pravaz, a French general surgeon, patented such a device. It has been recognized that the use of hypodermic needles, which activity is endemic in the field, is one particularly hazardous activity which could cause injury. More particularly, the use of a hypodermic needle in dentistry and other medical fields has been shown to put the operator at risk to inadvertent needle sticks presenting a potential high risk to infection disease transmission for health care workers.

Currently, there are several auto-retraction type syringes are known that provide increased safety by allowing the protruding needle to be retracted into a protective sheath after use. However, current syringes require the use of a palm-thumb grasp during their use. This type of hand dexterity presents a potential risk of inadvertent needle stick during entry and withdrawal from the patient tissues. Other syringes are provided with removable caps. However, this configuration does not solve the problem in a satisfactory manner.

All of these prior art references have either one or more of the following deficiencies.

1) The use of a hollow needle that is rigidly affixed to the end of a syringe-, tubing or hand-piece. The protruding needle presents a risk of inadvertent needle stick to the operator.
2) Existing auto-retracting syringes and the like require the operator to use a palm-thumb grasp to operate. This structure creates an increased risk of inadvertent needle stick to the operator.
3) Existing auto-retracting syringes and the like require the operator to make use of the hand to physically retract the needle, thereby, making it difficult and cumbersome to perform.

Some prior art syringes and needles with sheaths or caps are disclosed in the following U.S. Pat. Nos.: 5,120,310; 5,188,613; 5,267,961; 5,389,076; 5,423,758; 5,578,011; 5,632,733; 5,637,092; 5,810,775; 5,030,209; 4,911,693; 4,900,310; 4,813,426; 4,795,432; 4,664,654; 4,695,274; 4,966,592; 4,747,831; 4,900,311; 5,411,487; 5,106,379; 5,713,873.

With the rise of infectious diseases, i.e., hepatitis and AIDS, protection of the health care workers has become a needed priority because, as indicated in the medical/dental literature, inadvertent needle sticks represent a significant risk to our health care providers. In the past 15 years regulatory agencies such as OSHA have attempted to improve the use and safety of needles in the health care industry further accentuating the need for an effective means of preventing needle sticks.

In addition, various medical organizations have suggested and several states have instituted rules for the protection of care givers while providing injections to patients. More specifically, rules have been promulgated requiring that injection needles on syringes be provided which can be easily removed prior to an injection and re-installed immediately after an injection.

The proposed invention has been designed to eliminate the potential of inadvertent needle sticks during and after use.

Another related problem addressed by the present invention pertains to the deflection or bending of needles as they are inserted into the tissues of a patient. This deflection occurs because the needle is usually flexible because of its relatively small cross-sectional area and cannot resist effectively the axial and radial forces present during the insertion. The deflection is undesirable because it provides additional resistance during the insertion, to the movement of the needle and makes it difficult to guide the needle to a particular site. Moreover, if a needle is deflected, bent or otherwise deformed during insertion, it may cause more pain to the patient, trauma to the local tissues and other undesirable effect. It has been discovered (as disclosed in copending provisional application serial No. 60/173,374 filed Dec. 28, 1999), incorporated herein by reference, that these disadvantages are eliminated or at least alleviated if the needle is rotated about its longitudinal axis as it is advanced along the axis into the patient tissues. While rotating devices are known which rotate about their longitudinal axes to allow drilling through bony tissues, these devices do not allow high level tactile control during use. Other syringes do not allow the use of a bi-directional rotational insertion technique to be used during a power assisted injection process.

OBJECTIVES AND SUMMARY OF THE INVENTION

In view of the above-mentioned disadvantages of the prior art, an objective of the, present invention is to provide an injection device having a needle which can be selectively advanced from a retracted position in which the needle is hidden, toward an open position in which a therapeutic agent can be administered effectively, and can be retracted back to the retracted position before disposal.

A further objective is an injection device adapted to provide injection to a selected site and/or tissue by using a selective bi-directional rotational movement of the needle to prevent deflection of the needle.

Yet another objective is to provide an injection device which allows an operator to advance a needle at a manually controlled rate and with a hand-piece which is held steadily in a relatively stationary position with respect to the patient.

A further objective is to provide an injection device which can be used repeatedly to advance and retract a needle in a linear, rotational or bi-directional rotational motion.

Other objectives and advantages of the invention shall become apparent from the following description.

Briefly, an automatic injection device constructed in accordance with this invention includes a source of fluid to be injected, a needle, handle with a housing and a coupling used to selectively advance the needle out of the hand-piece, preferably under the control of the operator, and once an injection is complete, to retract it back into the hand-piece. Advantageously, the needle may be protracted and retracted several times during multiple uses on the same patient. The device may be a drug delivery device which serves to inject medicament from a tank or reservoir. This includes but should not be limited to infusion type pumps, syringe pumps, such as the Wand® made by Miiestone Scientific of Orange, N.J.

In one embodiment, of the invention, a spring is provided in the housing which is arranged to bias the needle. Preferably the needle is biased toward its retracted position so that if the needle is advanced to extend outwardly of the housing and then released, it automatically returns to the retrieved position within the housing thereby reducing the likelihood that the needle pricks or otherwise injures an operator, the patient, or anyone else. Locking members are also provided which are used to secure the needle in the first—that is— the retrieved position, or the second position. The coupling may be arranged and constructed to cooperate with the housing so that as the needle is advanced out of the housing, it is automatically and simultaneously rotated about its longitudinal axis. Typically, the needle may be rotated by about 45–270°. Preferably the needle is rotated by about 180°. This may be accomplished, for instance, by providing a helical groove on an inner surface of the housing and a boss on the coupling. As the coupling moves through the housing, its boss rides through the groove and this caming action causes the coupling, and the needle to rotate. If the groove is oriented in the same direction, the rotational motion is uni-directional. The groove can also be made to change direction one or more times along its length, in which case the needle undergoes a bi- or multi-directional motion. The term uni-directional is used to describe motion in the same sense, e.g., clockwise or counterclockwise. The term bi-directional is used to describe a motion that changes sense, e.g., initially clockwise, then counterclockwise.

Rotation may also be imparted to a needle affixed to a standard syringe. In this case, the needle is mounted to one wall of the barrel using a ball-bearing mounted, or other frictionless surface. A plunger is coupled to the other side of the barrel in a manner which forces the plunger to rotate as it is inserted into the barrel to force liquid from the barrel to be ejected through the needle. The plunger and the needle are coupled so that the rotation of the plunger is transmitted to the needle.

BRIEF DESCRIPTION OF THE FIGURES

FIG. 2 shows a sectional somewhat diagrammatic view of the hand-piece for the device of FIG. 1 with the needle in an extended position;

FIG. 3 shows a sectional view similar to FIG. 2 with the needle in the retracted position;

FIG. 4 shows a sectional view of the needle and a spring used to bias the needle toward the retracted position;

FIG. 5 shows a sectional view of the needle and the spring in the extended position;

FIG. 8 shows an enlarged view of the needle coupling and its engagement with a spiral groove;

FIG. 9 shows an enlarged side view of the coupling;

DETAILED DESCRIPTION OF THE PREFERRED EMBODIMENT

Figure 1:
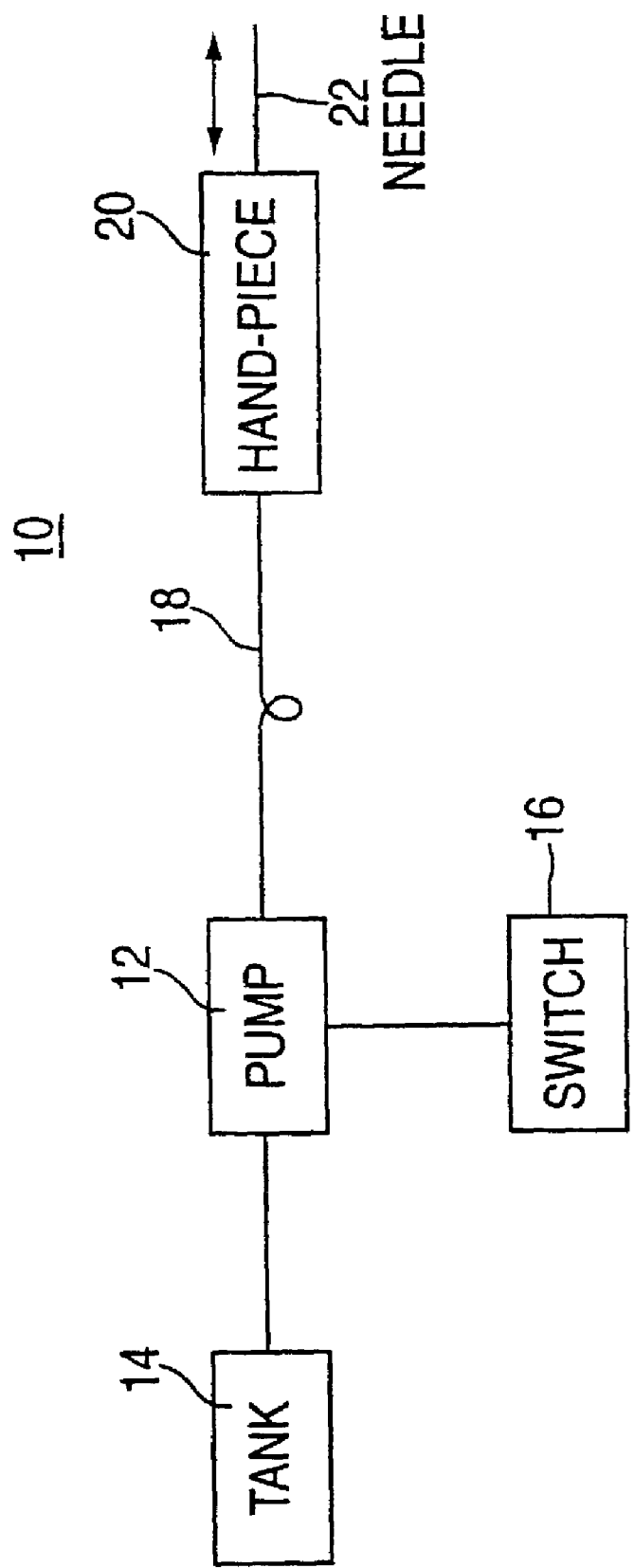
FIG. 1 shows a somewhat schematic diagram of an automatic injection device constructed in accordance with this invention.

In order to better understand the purpose of this invention, a somewhat generic automatic injection device is first described. In this application the term automatic injection device, as illustrated in FIG. 1 refers to a device 10 in which a fluid ejection means such as a pump 12 is used to force a fluid from a tank 14 under the control means such as a switch 16 into a flexible tubing 18. The tank may be a vial, a carpule or other known vessels that could be used to store a therapeutic liquid. The tubing 18 terminates in hand-piece 20 with a needle 22. The various elements described so far cooperate to allow a nurse, physician, dentist and other health care professional operator to inject selectively the liquid from tank 14 into the tissues of a patient (not shown) by activating the switch 16.

Importantly, according to this invention, the needle 22 is movable into and out of the hand-piece 20. In a preferred embodiment, the needle 22 is normally disposed inside the hand-piece 20 and is extended by the operator prior to or simultaneously with the injection. After the injection is complete, the needle 22 is preferably retracted into the hand-piece 20. In this manner, the needle 22 is exposed only the short periods of time that the injection actually occurs, thereby preventing injury and infection to the operator of the device 10 or other people. Studies have shown that a person handling a device associated with a needle is injured during this period.

Advantageously, the hand-piece 20, needle 22 and the tubing 18 are generally disposable. Moreover, the cap normally provided to cover the needle is eliminated, so it is no longer required.

Details of the hand-piece 20 and needle 22 are now discussed in conjunction with FIGS. 2–9. The hand-piece 20 includes in accordance with this invention a cylindrical housing 24 with an internal wall 26, an external wall 28, and two ends 30, 32. Hand-piece 20 further includes an elongated hollow stem 34 provided to protect the tubing 18. The tubing 18 which extends through the stem 34 into the housing 24 and is coupled directly or indirectly to the needle 20 as discussed more fully below. Stem 34 may be glued to the housing 24, or may be sized and shaped to form an interference fit therewith, whereby it can be inserted into the housing 24 or removed at will.

Mounted on housing 24 there is a control member such as a button 36 slidable in a longitudinal slot 38 extending through the housing. Housing 24 is provided with a stop 40 at the forward end of slot 38. The rear end 42 of the housing 24 serves as a rear stop for button 36. Alternatively, a stop similar to stop 40 may be provided on the external wall 28 of housing 24. Button 36 includes two spring arms 44, 46. These arms extend in the longitudinal axis of the housing 24 and are turned upward, or away from surface 28 at their tips. These arms 44, 46 are somewhat flexible and cooperate with the stop 40 and end wall 42 to limit the movement of button 36 in slot 38. More particularly, as button 36 is reciprocated by an operator in slot 38, when the button reaches its forward position, the arm 44 rides over the stop 40 and then snaps radially inward to form an interference fit with the stop 40. This position (shown in FIG. 2) corresponds to the extended position of the needle 20, with the button 36 being locked. The button 36 can be released by pressing it downward toward the housing 24, thereby causing arms 44, 46 to flex upward. The button 36 can then move backward, away from the front opening 30 because the arm 44 clears the stop 40. When the button 36 is moved backwards toward stem 34, when its rear arm 46 engages the rear wall 42, the button 36 is locked into the rear position, and the needle 22 is in its fully retracted position, as indicated in FIG. 3.

Button 36 further includes a pin 48 extending downwardly or radially through slot 28 to engage needle 20. Button 38 can be made of a high impact plastic material. Its wings 44, 46 can be made integral with the button 38, or can be made of steel.

Referring now to FIGS. 4 and 5 (in which the stem 34 has been omitted for the sake of clarity) the needle 20 is attached to a coupling 50. This coupling includes a central hollow shaft 52 sized and shaped to connect to an end of tubing 18. Preferably the tubing 18 is glued or otherwise secured to the shaft 52 so that it is permanently mounted thereto.

The coupling also has a circular disc 54 mounted coaxially on the shaft 52. Spaced axially away from disc 54 there is cup-shaped adapter 56. Adapter 56 has an outer surface 58 with a plurality of axially shaped circumferential ribs 60. The disc 54 and adapter 56 are separated by an annular space 62 having an axial length which is equal to, or slightly greater than the cross-sectional dimension of pin 48. The button 36 is positioned on the housing 12 so that this pin 48 extends into the space 62 as shown. Therefore the coupling 50 and the button 36 are effectively interlocked so that the coupling 50 can be moved in either direction along the length of the housing 24 and the button 36 will move with it (within the length of the slot 38) and vice versa. However, because space 56 is annular, the coupling 50 may also rotate around the longitudinal axis of housing 24 without interference from button 36.

Typically, needle 22 includes a narrow, thin-walled hollow shaft 64 and a base 66. In one embodiment of the invention the needle 22 is configured with the base 66 being mounted on shaft 52 so that it abuts the adapter 50. Base 66 is preferably bonded or otherwise secured to the shaft 52 and/or the adapter 56. The base 66 is hollow and in communication with the opening in the hollow shaft 64. Therefore, once the base 66 is mounted and secured to the adapter 56, the interior of tube 18 is in communication with the interior of the shaft 64 through the shaft 52.

Preferably, the end 30 is partially closed with a disc-shaped end wall 68. This end wall 68 has an opening (not shown) sufficiently large to allow the needle 22 and its base 66 to extend at least partially from housing 24, as seen in FIG. 5.

In one embodiment of the invention, as mentioned above, the base 66 is bonded to adapter 54. In another embodiment of the invention, the adapter 54 is a female Luer connector and the base 66 is a male Luer connector, the two connectors cooperating to mount the needle 22 on the coupling 50 so that the needle 22 can be attached and removed at will. This feature may be advantageous during a long procedure the tip of the needle 22 may become dull and may have to be changed before the procedure is complete.

In another embodiment of the invention, an optional compression spring 70 is provided between the end wall 68 and the coupling 50 in such a manner that normally the spring 70 pushes the coupling 50, and the needle 22 attached thereto, away from wall 68. In other words, in this embodiment, the spring 70 urges the needle 22 toward its retracted position.

Figure 6:
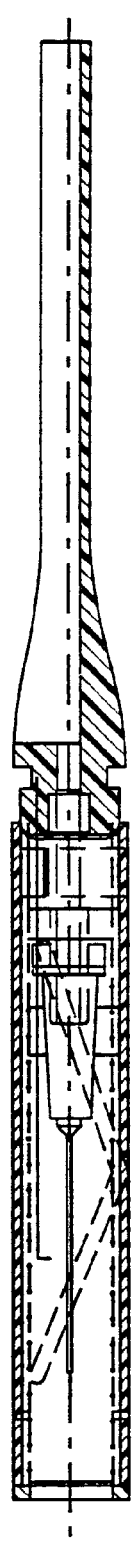
FIG. 6 shows an embodiment of the invention which allows the needle to rotate about its axis, the needle being in a retracted position.
Figure 7:
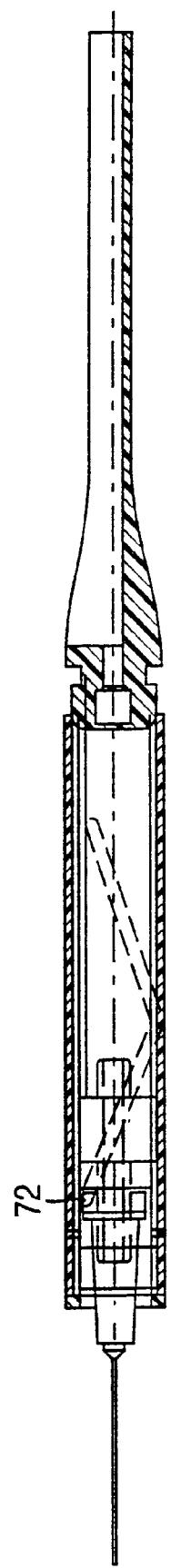
FIG. 7 shows a view similar to FIG. 6 with the needle being in the extended position.

Yet in a further embodiment of the invention, shown in FIGS. 6, 7 and 8, the coupling 50 is provided with a boss 72 extending radially, and the inner surface 26 is provided with a helical groove 74, with the boss 72 being seated with the groove 74 as shown. In this embodiment, coupling 50 and the needle 22 attached thereto are rotatable about the longitudinal axis of housing 24. Coupling 50 with its boss 72, and groove 74 define a rotating member that cooperate with the button 36 so that the translational movement of button 36 along the housing 24 in slot 38 causes a simultaneous translation and rotation of the needle 22 as the needle moves between its retracted and protracted positions.

The operation of device 10 is now described in conjunction with the drawings. Initially, it is assumed that device 10 has a hand-piece which has been provided with a spring 70 and groove 74. Prior to an injection the needle 22 is disposed in the hand-piece 20 in its retracted position and is maintained in this configuration by the spring 70. In fact the tubing 18, hand-piece 20 and needle 22 may come in a kit, several kits being made available for the operator, each with a needle having a shaft 64 of different nominal lengths (i.e. 20 mm, 25 mm, 30 mm . . . ) In one mode of operation, the operator initializes the pump 12, positions the hand-piece 20 so that the hand-piece points to the site or tissue of interest, activates the switch 16 to start the delivery of the therapeutic agent, and starts advancing the needle 20 to cause the needle to slowly extend outwardly of the hand-piece and coaxially with the longitudinal axis of the hand-piece 20. Preferably, the hand-piece is sized and shaped so that it can be held by the operator in the manner of a pencil with his forefinger being free to rest on and push the reciprocate button 36. However, before the needle can be pushed forward, it must be unlatched because it is locked in the retracted position by the cooperation between arm 46 and rear wall 32. Therefore the operator must release the needle 22. This can be accomplished by pushing down or radially inwardly on the button 36. This action causes the button 36 to bend arms 44, 46 upward thereby releasing arm 46 from rear wall 32. The needle 22 is now free to move forward.

As the needle 22 is advancing with respect to the hand-piece 20, the boss 72 rides in a caming action against the helical groove 74 and causes the coupling 50 and the needle 22 to rotate. This combined advancement or translation of the needle and its simultaneous rotation is continued until the button 36 reaches the forward stop 40. At this point the forward arm 44 goes over the stop 40 and then forms an interference fit with it causing the button 36 and the needle 22 to lock in the extended position. This action is felt by the operator as a click and therefore the operator does not have to keep his eye on the hand-piece. Since the needle 22 has now been locked in the extended position, the operator can release button 36 and continue the injection without moving the needle. The therapeutic liquid from tank 14 is injected into the patient during or after the needle has been advanced out of the housing 24 and into the patient's tissues.

In some situations, an operator may prefer to advance the needle 22 out of housing 24 before inserting the needle into the tissues. In this case he just moves the button 36 forward while he keeps the hand-piece 20 away from the patient until the needle 22 reaches its extended position and is locked into this position. The operator can proceed to insert the needle 22 into the patient tissues in a normal manner.

Once, the injection is completed, the needle 22 can be retrieved back into housing 24. This retrieval may be accomplished either while the needle is imbedded into the patient's tissues, or after it has been withdrawn therefrom. In either case, the needle 22 can be retrieved by pushing the button 36 inwardly or radially causing the arm 44 to rise and disengage from the forward stop 40. Once the arm 44 is disengaged, the operator can release button 36. Since spring 70 is in a compressed state, as shown in FIG. 5, releasing the button 36 causes the spring 70 to extend axially through the housing 24 forcing the coupling 50 to move rapidly backward toward stem 34. Retraction occurs by rotation about the long axis. Rotation minimizes drug resistance and makes the retraction more efficient. In this manner, the needle 22 which is attached to the coupling also moves rapidly backwards and snaps back into the housing to the retracted position. This operation takes places very fast thereby avoiding any chance that the operator will get pricked or otherwise injured by the sharp tip of needle 22. Since the end of tubing 18 is also attached to the coupling, the tubing 18 slides through the stem 34 and in and out of the housing 24 as required.

If the spring 70 is omitted, the needle 22 must be retrieved into the housing 24 manually using button 36 causing the needle to rotate upon removal.

As illustrated in FIG. 4, the coupling 50 is provided with ribs 68 and disc 54 which arranged and constructed to slidably engage the inner wall 28 of housing 24. Therefore, as the coupling 24 reciprocates within the housing in a smooth controlled movement without any radial jitter, thereby giving the operator a solid feel and ease of operation.

Preferably, the tubing 18, hand-piece 20 and needle 22 are all disposable. Health regulation frequently require that disposable items with sharp tips or edges which may puncture an attendant must be disposed separately. As indicated in FIG. 9, preferably the portion of the shaft 52 extending between disk 54 and adapter 56 is provided with a radial groove 76 which may be about 0.015" deep. At the end of the injection procedure, the stem 34 may be removed from the housing 24, and the housing 24 may be bent manually to cause the coupling 50 to snap along groove 76. The disc 54 can now be removed from the housing 24 while the adapter 56 and the needle 24 are retained in the housing 24 by the pin 48. The housing 24 with the needle 22 can now be disposed as a sharp object while the remaining portions including tubing 18, stem 34 can be disposed as standard (i.e., non-sharp) objects.

In the Figures, the groove 70 is shown as being uni-directional so that as the needle is advanced, it is rotated by the groove always in the same direction, e.g, clockwise. In an alternate embodiment, the groove can be made into axially spaced segments with adjacent segments being oriented in different senses. For this arrangement, as the needle is translated along its axis, it is simultaneously rotated first in one direction, then in the opposite direction by the respective groove segments. This the needle can have a uni-directional, bi-directional or multi-directional rotation.

Figure 10:
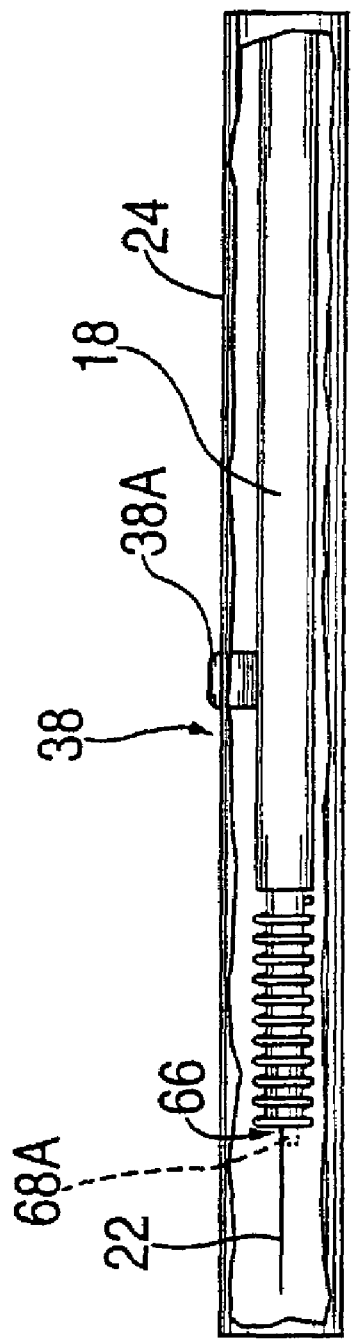
FIG. 10 shows a side view of a hand-piece according to an alternate embodiment of the invention wherein the helical groove has been omitted.
Figure 11:
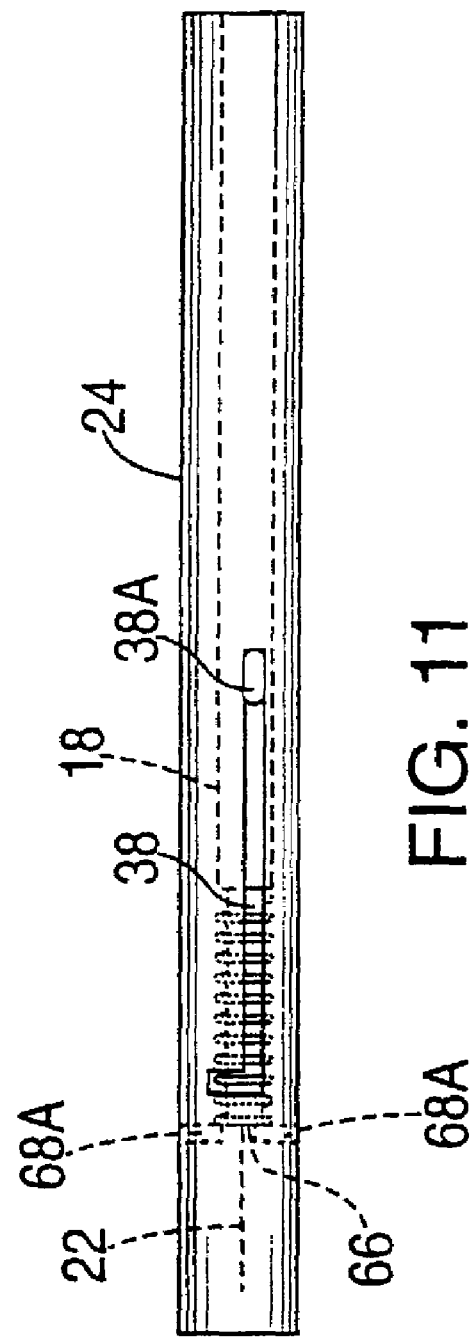
FIG. 11 shows a top view of a hand-piece according to an alternate embodiment wherein the slot holding the button or tab has side wing or wings.
Figure 12:
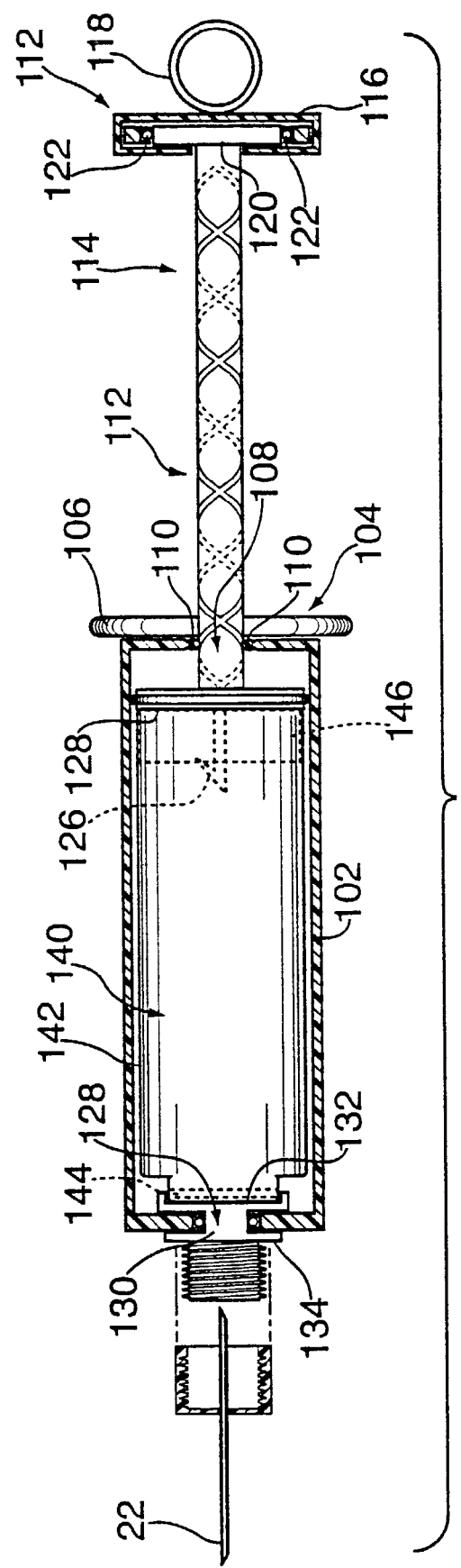
FIG. 12 shows a sectional view of a hand-piece according to an alternate embodiment of the invention

As discussed above, the helical groove 74 is optional. If it is omitted, then the coupling 50 can have a much simpler shape, or can be eliminated altogether. For example, FIG. 10 shows an embodiment wherein the tubing 18 abuts the base 66 of needle 22. The button 36 or in this case, a simple tab 38A extends through slot 38 and is engaged to the tubing 18. Instead of an end wall 68, or in addition thereto, an annular spring stop 68A is provided on the inner wall 28 of housing 24. Spring 70 is in compression between this stop 68A and the base 66 of needle 22. If the housing 24 is made without the groove 74, as shown in FIG. 10 then the needle 22 can be advanced and retrieved linearly, i.e., without imparting to it any substantial rotary motion about its longitudinal axis.

In the embodiments of FIGS. 1–9, the button 36 is limited to a longitudinal motion by the shape of slot 38. FIG. 10 shows an alternate embodiment of the invention. In this embodiment, the button 36 or a tab is disposed in a longitudinal slot 36A having a lateral extension 38B. In this embodiment, after the needle 22 reaches its extended position, the operator shifts the button 36 into lateral extension 38B. The force of spring 70 applied to the base 66, and hence to tubing 18, forces the needle to be locked in this position until it is released. If desired, a second lateral extension 68C may also be added to park the needle in the retreated position so that it does not move.

In the embodiments of FIGS. 1–11 a liquid injecting device 10 is described wherein liquid from a separate tank is pumped through a flexible tubing 18 and hand-piece 20 to needle 22. In an alternate embodiment of the invention, some of the novel features of device are incorporated into a standard syringe-type liquid delivery system. In this embodiment, a syringe 100 is provided having a barrel 102 having a first end wall 104 with finger tabs 106. A hole 108 is made in the wall with two opposed radial arms 110. Extending through hole 108 there is provided a plunger 112 formed of a rod 114. At one end, rod 114 is formed with a head 116 and a thumb ring 118. Inside head 116 there is a stationary disc 120 and bearings 122 attached to rod 114. Rod 114 is formed with one or more helical grooves 124.

At the opposite end, rod 114 is formed with a harpoon 126. Next to the harpoon, there is a piston 130 with an O-ring 132 and being attached to rod 114.

At the other end of barrel 102, there is provided an end wall 126 with an opening 128. A sleeve 130 passes through the opening 128 and is provided with two disc-shaped walls 132, 134. Ball bearings or other frictionless couplings support the sleeve 130 and walls 132, 134 on end wall 126 in a rotatable manner. A connector 136 is mounted on wall 134 to receive needle 22. When the needle 22 is mounted on connector 136 by its base 66, a portion 22A of the needle extends into the barrel 102.

The syringe 100 is used to eject a liquid such as an anesthetic disposed in a cartridge 140. This cartridge 140 includes a glass cylindrical housing 142, with a membrane 144 at one end and a rubber stopper 146 at the other end.

The end wall 104 on syringe 100 is removable to allow the cartridge 140 to be inserted into the barrel 100 with the membrane 144 disposed near end wall 126 and being engaged by wall 132. Once the cartridge 140 is inside the barrel and an operator is ready for the injection, the operator mounts the needle 22 on connector 136, its portion 22A enters into the barrel 102 and penetrates the membrane 144. Next, the end wall 104 is replaced on the barrel so that the harpoon 126 penetrates and engages the stopper 146. The operator then starts the injection by pushing the needle 22 forward to penetrate the subject tissues. During the forward movement of the needle, the operator holds the syringe with two fingers on the tabs 106 and the thumb engaging ring 118 and pushing the rod forward. During this motion, the rod is slowly advanced into the barrel 102, forcing the piston into the housing 142. The piston and the stopper both move forward expressing liquid from the cartridge 140 through the needle 22. Importantly, the positioning of the groove(s) 124 and tabs 110 in opening 108, the caming action of tabs 110 on groove(s) 124 causes the rod 114 to rotate around its longitudinal axis, which also coincides with the longitudinal axis of the barrel 102. The rotation of the rod 114 is transmitted by the harpoon 126, piston 128 and O-ring 130 to the cartridge 140 and then through the end wall 132 to needle 22. Thus the needle 22 rotates essentially in the same manner as the rod 114.

The rotation imparted to the needle 22 attached to either hand-piece 20 or syringe 100 is dictated by the pitch and length of the grooves 74 and 124 respectively. It has been found that preferably, the needle through its travel should rotate by about 45–270°. More particularly, it has been found that the rotational movement is most effective when it covers about 180°.

An important advantage of the present invention, is that it allows a clinician to hold the hand-piece within a grasp similar to one used for holding a pen or pencils, i.e., between the thumb, the forefinger and the middle finger. Traditional grasps for injection devices, such as standard syringes, involve the use of the fore- and middle finger holding the barrel and the opposed thumb moving toward the fingers and applying pressure on the piston. This grasp is not very efficient because it is difficult for a clinician to hold a syringe steady or to advance it at a slow, controlled rate while the fingers are moving toward each other. Moreover, it is believed using this process repeatedly over several hours a day may cause carpal syndrome. On the other hand, in the present invention, the hand-piece is held between the thumb and the middle finger. The forefinger is used to steady the hand-piece, to direct it more precisely toward the desired tissues and to move the needle. Thus, the present invention provides a much more ergonomic device.

The subject invention discloses of a novel approach for injection systems in which a needle can be presented to the patient in a retracted state, thereby protecting the operator prior to the entry of the needle into patient tissues. Once the injection procedure has been concluded the needle can be withdrawn automatically back into the protective housing prior to having the hand-piece being moved away from patient's tissues, thereby eliminating the exposure of the operator to the unprotected needle at all times.

The novel design allows the reuse of a needle on a particular patient, i.e., subsequent dental injections during the same appointment can be given for a patient using the same device.

The subject invention provides the following advantages over the prior art:

A. Allows the needle to automatically retract into the protective housing.

B. Allows the operator to advance the needle out of the housing sheath via manual operator control.

C. Allows the operator to use a pen-like grasp which has been shown to have superior tactile control and more ergonomic then existing configurations.

D. Does not require extensive hand manipulation or the use of the second hand to automatically retract the needle.

E. Allows for reuse of the needle on the same patient during a given procedure, but eliminates the risk associated with the re-use of a needle.

F. Depending on the structure of the hand-piece, the needle can be subjected to a translational motion or a simultaneous translational and rotational motion.

G. Depending on the structure of the hand-piece, the needle can be subjected to uni-directional, bi-directional or even multi-directional motion.

H. The injection process described can be repeated several times of necessary with ease, with the same or a different needle.

This invention represents a major advancement in the safety and use of hollow-core needles. It discloses a device that is easy and predictable in operation. The device minimizes or eliminates the risk potential of inadvertent needle sticks to health care workers.

While several embodiments have been described it should be understood that other modifications can be made to the invention without departing from its scope as defined in the appended claims.

We claim:

1. An injection system for injecting a liquid such as a therapeutic agent into a patient, said system comprising:
   a source of liquid;
   a hand-piece remote from said source and adapted to be held by the operator during an injection procedure;
   a coupling having a first, a second end, and a grove disposed therebetween:
   a tubing connected to said second end;
   said hand-piece including a hollow housing and a needle supported by said housing and having a first position wherein said needle is disposed in said housing and a second position in which said needle is disposed at least partially outside said housing to provide the injection, said needle being coupled to said first end of said coupling; and
   a control member disposed on said hand-piece and coupled to said coupling;
   wherein said needle is selectively movable between said first and second positions by said control member; and wherein said handpiece and said coupling cooperate to cause said needle to translate and rotate simultaneously as said needle is moved along at least a substantial portion of the path between said first and second positions to prevent said needle from bending; and wherein said coupling is breakable along said groove to allow said tubing to be removed from said hand piece and leaving said needle trapped within said hand-piece.

2. The system of claim 1 further comprising a first stop cooperating with said handle to secure said needle in said first position.

3. The system of claim 2 further comprising a second stop cooperating with said handle to secure said needle in said second position.

4. The system of claim 1 further comprising a spring biasing said needle toward one of said first and second positions.

5. The system of claim 4 wherein said spring bias said needle toward said first position, whereby when said needle is released from said second position it automatically returns to said first position.

6. The injection device of claim 1 wherein said housing includes a longitudinal slot and a button sliding in said slot, said button being coupled to said needle to move said needle between said first and said positions.

7. The injection device of claim 6 further comprising a first locking element that cooperates with said housing to lock said needle in said first position.

8. The injection device of claim 7 further comprising a second locking element cooperating with said housing to lock said needle in said second position.

9. The injection device of claim 8 wherein said button cooperates with one of said first and second locking elements to release said needle from said first and second positions, respectively.

10. The injection device of claim 6 further comprising a spring disposed in said housing, said spring being arranged to bias said needle toward one of said first and second position.

11. The injection device of claim 10 wherein said spring is arranged to bias said needle toward said first position whereby said needle automatically returns to said first position when released from any position external of said housing.

* * * * *